(12) United States Patent
Sparr (10) Patent No.: US 11,806,271 B2
(45) Date of Patent: Nov. 7, 2023

(54) DEVICE AND METHOD FOR DETERRING AN UNDESIRABLE SLEEPING POSTURE

(71) Applicant: Jennifer Sparr, San Antonio, TX (US)

(72) Inventor: Jennifer Sparr, San Antonio, TX (US)

(*) Notice: Subject to any disclaimer, the term of this patent is extended or adjusted under 35 U.S.C. 154(b) by 217 days.

(21) Appl. No.: 16/673,568

(22) Filed: Nov. 4, 2019

(65) Prior Publication Data
US 2020/0129323 A1 Apr. 30, 2020

Related U.S. Application Data

(63) Continuation of application No. 14/325,473, filed on Jul. 8, 2014, now Pat. No. 10,463,529, which is a continuation-in-part of application No. 13/669,161, filed on Nov. 5, 2012, now abandoned.

(60) Provisional application No. 62/002,258, filed on May 23, 2014, provisional application No. 61/555,501, filed on Nov. 4, 2011.

(51) Int. Cl.
*A61F 5/56* (2006.01)

(52) U.S. Cl.
CPC ........................................ *A61F 5/56* (2013.01)

(58) Field of Classification Search
CPC ...... A61F 5/00; A61F 5/37; A61F 5/56; A61F 15/008; A61F 2013/00165; A41D 10/00; A41B 13/065; A61B 90/00; A61N 2005/1097
USPC ........ 128/845, 846, 848, 869–871; 602/902; D24/190
See application file for complete search history.

(56) References Cited

U.S. PATENT DOCUMENTS

| | | | | |
|---|---|---|---|---|
| 2,304,235 A | * | 12/1942 | Boots | A61F 5/56 116/1 |
| 2,367,690 A | * | 1/1945 | Purdy | A61F 15/006 128/888 |
| 4,212,296 A | * | 7/1980 | Schaar | A61F 13/063 602/42 |
| 5,144,958 A | * | 9/1992 | Krueger | A61F 15/008 600/556 |

(Continued)

*Primary Examiner* — Caitlin A Carreiro
(74) *Attorney, Agent, or Firm* — William H. Quirk; Alexander J. Antonio; Rosenthal Pauerstein Sandoloski Agather, LLP (57) ABSTRACT

Domed articles are disclosed with reinforcements and adaptations for adhesively-applying them to a person's body while sleeping, to deter against the person from assuming an undesirable sleeping posture, which may include a posture that is commonly associated with louder and more dangerous snoring. The dome-like articles (1) are typically shaped like a campaign hat in that they have a central dome (or crown region) surrounded by a concentric, relatively-flat annular perimeter (or brim region), (2) have a hypoallergenic adhesive on a flat side of the brim—the side facing the person's body—for removably securing the domed article to the person's body, (3) are typically formed from a unitary plastic sheet with complex shapes and surface features that reinforce the strength of the dome to resist collapse when the person rolls onto it, such shapes and features including stress distributors and structural reinforcements such as intersecting arcuate ridges and/or troughs, and (4) typically have holes or other surface features to allow for ventilation of the space enclosed between the dome and the person's body.

19 Claims, 10 Drawing Sheets

(56) References Cited

U.S. PATENT DOCUMENTS

| | | | | |
|---|---|---|---|---|
| 7,988,673 B2* | 8/2011 | Wright | ............... | A61F 15/004 |
| | | | | 604/174 |
| 2007/0129664 A1* | 6/2007 | Fuchita | ............... | A61N 1/0448 |
| | | | | 604/20 |
| 2007/0256695 A1* | 11/2007 | Crocetti | ............... | A61F 5/56 |
| | | | | 128/848 |
| 2007/0283962 A1* | 12/2007 | Doshi | ............... | A61M 16/106 |
| | | | | 128/206.18 |

* cited by examiner

DEVICE AND METHOD FOR DETERRING AN UNDESIRABLE SLEEPING POSTURE

CLAIM OF PRIORITY TO PRIOR APPLICATIONS

The present application is a continuation of previously filed, co-pending U.S. Non-Provisional application Ser. No. 14/325,473, filed Jul. 8, 2014, which claims the benefit of previously filed U.S. Provisional Application, Ser. No. 62/002,258, filed May 23, 2014, and is a continuation-in-part of U.S. Non-Provisional application Ser. No. 13/669, 161, filed Nov. 5, 2012, which claims the benefit of previously filed U.S. Provisional Application, Ser. No. 61/555, 501, filed Nov. 4, 2011. The full disclosures, including the claims and drawings, of all of the aforementioned applications are incorporated by reference into the present disclosure as though now set forth in their entirety.

BACKGROUND OF THE INVENTION

1. Field of the Invention

The present invention relates to the field of body positioning aids for encouraging the human body to assume a safe and healthy posture while sleeping and, more particularly, for encouraging a posture that tends to minimize snoring for people who tend to snore.

2. Description of Related Art

Snoring, needless to say, can be annoying to others in the same bed, to others in the same house, and occasionally even to others living next door. The health of those who snore can also be at serious risk—not just when they get kicked, shoved or smothered by their sleeping companions—but often due to sleep apnea and/or reduced blood-oxygen levels that may be associated with snoring.

It has long been known that many people snore more commonly or more loudly and dangerously when they sleep lying on their backs. Snoring and obstructive sleep apnea are at much greater risk when they sleep on their backs, largely because the tongue and the muscles and surrounding tissue in the throat typically relax during sleep. When people are in a relaxed sleep state, if they are already on their back or if they roll or move onto their back, the relaxed tongue and throat tissue tends to slump backwards to partially block the airway to their lungs. The air they are breathing necessarily speeds up as it moves through the smaller, blocked opening of the airway, and the fast-moving air then causes the loose surrounding tissue to vibrate, which causes the noise that we call snoring. As a result, those who live with loud snorers quickly learn to nudge the snorer into another position in order to stop or reduce the snoring.

Likewise, numerous innovative problem solvers have developed devices and methods for keeping people from sleeping on their backs and from rolling or moving into a back-lying position while they sleep. Perhaps most famous, many have long known about the approach of sewing a tennis ball into the pocket of a T-shirt and having a snorer wear the tennis ball shirt backwards when they sleep, which keeps them off their back because it is uncomfortable to sleep on a tennis ball. Many others have long tried to resolve snoring challenges with variations on that ancient ball-sewn-in-a-pocket concept, such as is shown, for example, in U.S. Pat. Nos. 2,304,235 and 5,893,365.

Unfortunately, despite that problems with snoring have been common since the dawn of time, and despite that many have long been trying to resolve such problems, few have succeeded in developing an affordable solution that works well on a consistent basis.

DETAILED DESCRIPTION OF PREFERRED EMBODIMENTS

Figure 1:
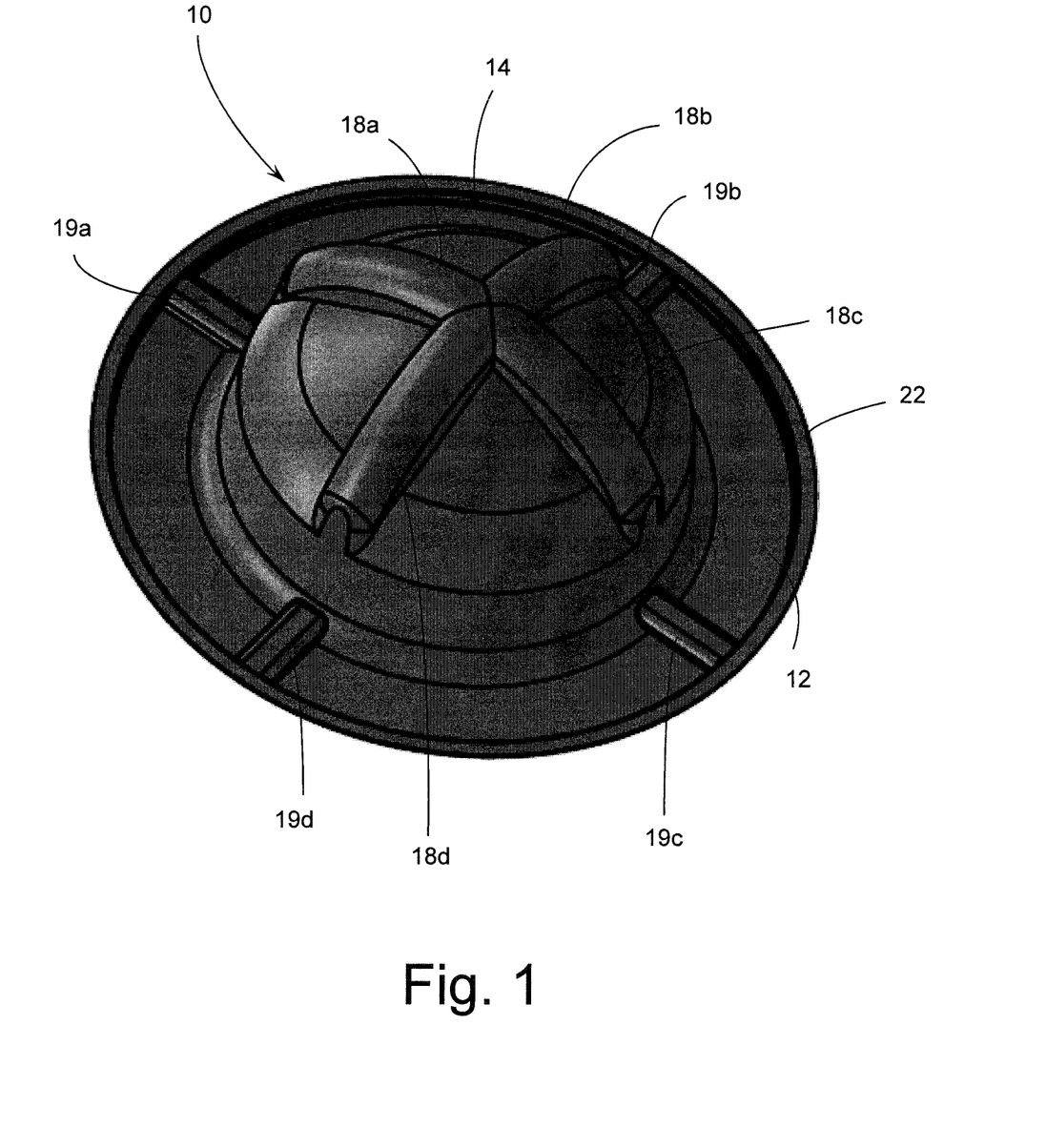
FIG. 1 is a perspective view of a preferred embodiment 10 of the device of the present invention.

Reference is made first to FIG. 1 which provides a perspective view of a preferred embodiment of the device of the present invention constructed from a unitary molded plastic material. In the perspective view of FIG. 1, the various external features of the device are disclosed. Supine-deterrent 10 is generally seen to be a hat-shaped device, shaped similar to a campaign hat, sized and configured to be removably placed on the back of the person.

As described above, the basic purpose of the device is to consciously or subconsciously deter the person from sleeping on the person's back, a position which tends to increase the incidence and severity of snoring. Because snoring while sleeping is frequently associated with the orientation of the sleeper on the sleeper's back, the device of the present invention serves as a manner of reducing the incidence of snoring while sleeping. The structure of supine-deterrent 10 provides just enough of a conscious or subconscious distraction or discomfort as to cause the person to move into a position where such discomfort no longer exists or occurs. In general, this means moving from a position where the person's back is against the relatively firm surface of the sleeping platform (mattress) to a position where such contact is not being made. Further details regarding this functionality are described in conjunction with FIGS. 7A and 7B below.

Figure 3:
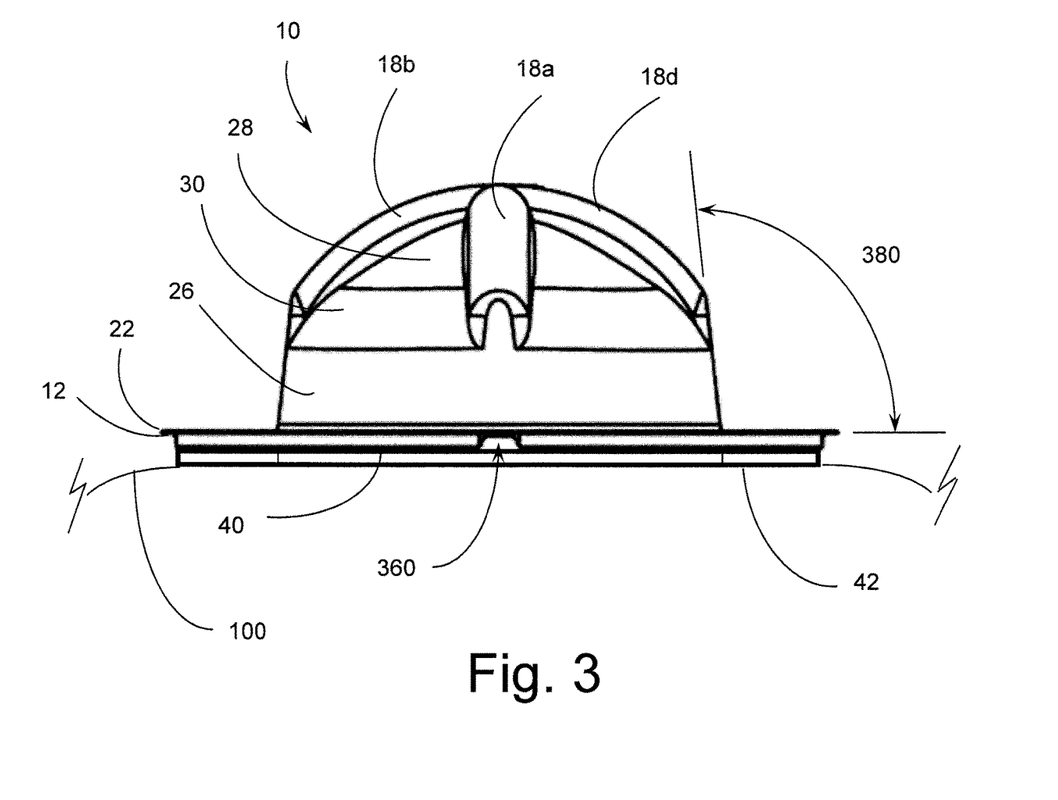
FIG. 3 is a side elevational view of the preferred embodiment 10 of the device of the present invention.

FIG. 1 shows in detail the various exterior structural features of supine-deterrent 10 that provide its rigidity, comfort, and ease of positioning and placement for use of the device. The overall hat-shaped configuration, similar to the shape of a campaign hat, of supine-deterrent 10 includes contact annulus 12 which is a relatively flat ring perimeter region that, on an underside surface (not shown), provides the contact point between the device and the skin surface of the person's back. Although FIG. 1 shows contact region 12 as a ring-shaped annulus 12, those skilled in the art will recognize that such contact region could be comprised of other shapes, including, but not limited to, a rectangle, an oval (such as represented by the embodiment of FIGS. 5, and 8-11), a square or an irregular shape. As best evident in FIG. 3, contact annulus 12 has a substantially planar lower surface 12a. The lower surface of contact annulus 12, shown in an unflexed position in FIG. 3, is completely planar; however, when the device of the present invention is in use on the back of a person, contact annulus will flex along the surface of the person's back. Thus, when the device is operatively positioned on the back of a person, contact annulus 12 is slightly less than planar so that contact annulus 12 may conform to the surface of the person's back which results in contact annulus 12 having a substantially planar lower surface. The manner of adhesively attaching the device of the present invention to the person's back is described in more detail below.

Extending concentrically within contact annulus 12 is reinforced dome region 14 of supine-deterrent 10. The dome region 14 in FIG. 1 is a generally spherical section, whereby the walls converge such that the space defined by the walls reduces at further distance from the relatively larger opening near the base of the dome. Those skilled in the art will recognize that the dome may not just be a spherical section but may also have other non-spherical shapes whereby the walls converge in an analogous manner. In the alternative embodiment shown in FIGS. 5 and 8-11, the dome may generally be shaped as an ovoid surface such that its walls 826 and 828 generally converge toward one another at distances further from its base 512. In still another alternative embodiment (not shown), the dome may be shaped as, or may include, a frustoconical shape wherein the walls of the dome analogously converge toward one another in linear relationship to the distance from the dome's base. A rectangular pyramid shape is used in further alternatives whereby the walls analogously converge toward one another in linear relationship to the distance from the dome's base and define a rectangular shape. Still other alternatives use other irregular shapes such that all the walls of the irregular shape analogously converge toward each other in linear relationship to the distance from the base of the dome structure.

For structural reinforcement of the dome shape, positioned near the center of reinforced dome region 14, are arcuate ridges 18a-18d. In the preferred embodiment of the present invention, arcuate ridges 18a-18d comprise long cylindrical convex elevations that together form a cross-shaped eminence centered on the apex of reinforced dome region 14 of the device. These arcuate ridges 18a-18d primarily provide structural strength to the dome shape of the device. Without such changes in the plane of the surface orientation, and therefore the wall structure of the dome-shaped device, there would be a tendency for the dome shape to collapse when a direct force might be exerted on the apex of the dome. Arcuate ridges 18a-18d, structured as shown, provide multi-directional structural support to what otherwise would be a flat or simple curve wall structure.

Flat ridges 19a-19d are orthogonally arranged around the upper surface of contact annulus 12. These flat ridges 19a-19d provide further structural support for reinforced dome region 14. Flat ridges 19a-19d are generally rectangular in shape and their raised character form airflow apertures 360, positioned along the lower surface of contact annulus 12 and described in further detail below.

Figure 2:
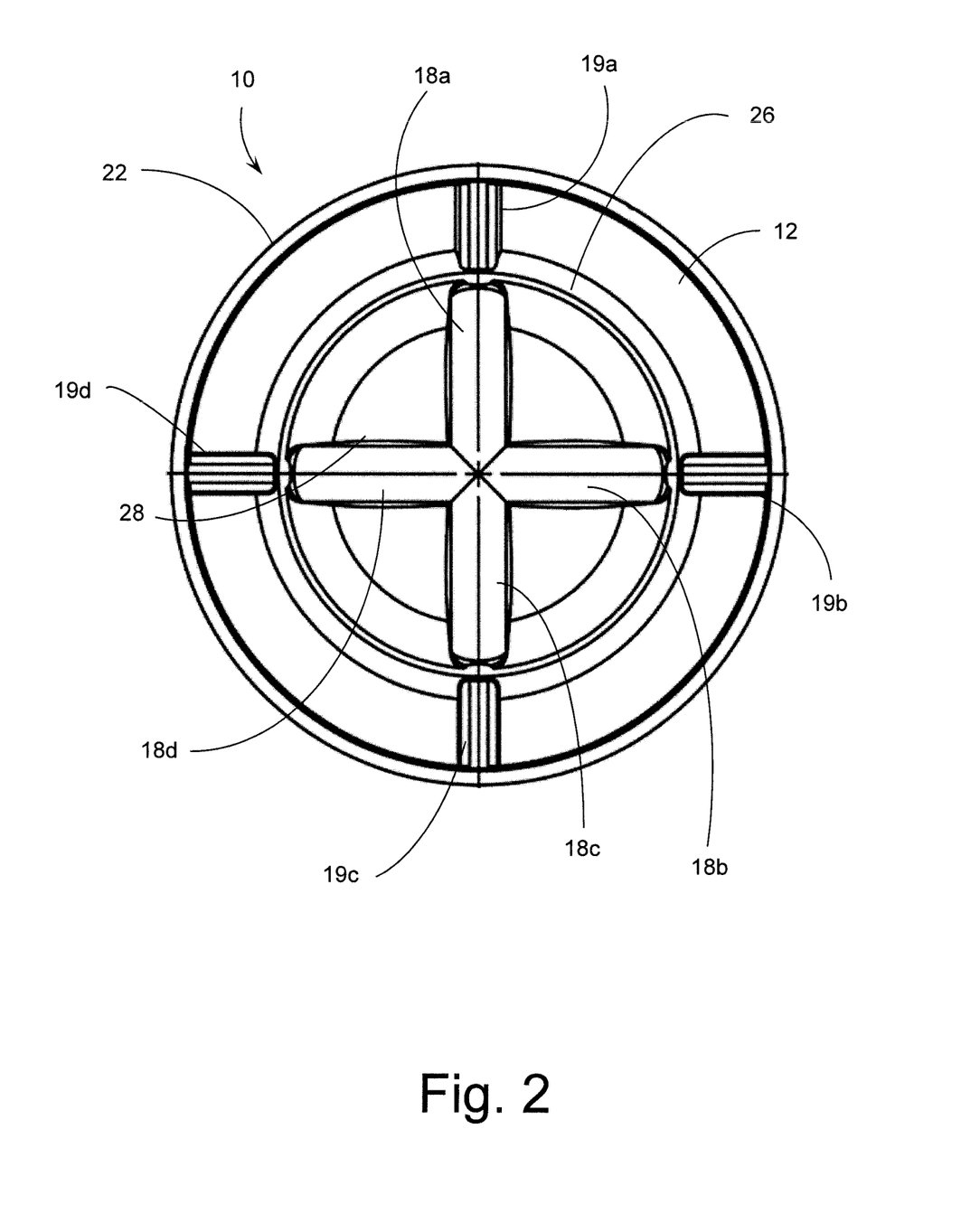
FIG. 2 is a top plan view of the preferred embodiment 10 of the device of the present invention showing the exterior structures of the device.

FIG. 2 is a top plan view of the preferred embodiment of the device of the present invention highlighting in greater detail the structures and contours of the various external features of the device as briefly described in conjunction with FIG. 1. In FIG. 2, supine-deterrent 10 is shown to be constructed from a generally circular-shaped device having contact annulus 12 as well as reinforced dome region 14 as described above. Along the peripheral edge of contact annulus 12 is perimeter flange 22. Forming reinforced dome region 14 are dome base walls 26 and dome top wall 28. Arcuate ridges 18a-18d are shown as they are positioned and configured within dome top wall 28.

Dome base walls 26 are shown below dome top wall 28 forming reinforced dome region 14. These dome base walls 26 provide the person with the ability to grasp the device using (for example) the thumb of the hand on one of the dome base walls, and the forefinger or two fingers of the same hand in the opposing dome base wall, in a manner similar to grip indentations 16a and 16b as shown in FIGS. 5, 8, 9 and 10. In this manner the person may slightly squeeze the device to grip it firmly for orientation positioning and placement on the person's back.

The device of the present invention is preferably molded from a lightweight but resilient plastic material, being die-stamped on a punch press from sheet stock of amorphous polyethylene terephthalate (APET) with a thickness of 0.0175 inches. Examples of other suitable plastics include high-density polyethylene (HDPE), polyvinyl chloride (PVC), low density polyethylene (LDPE), polypropylene (PP), high impact polystyrene (HIPS), acrylonitrile butadiene styrene (ABS), polycarbonate (PC), and polycarbonate/acrylonitrile butadiene styrene (PC/ABS). The important aspects of the material for purposes of the present invention are its weight and rigidity. The material should also have enough bending plasticity (i.e. not be brittle) to prevent the formation of sharp edges or cracking even under excessive crushing force. Additionally, the material should be resilient such that, in the event of collapse under force, the dome shape tends to flex back.

Reference is next made to FIG. 3 which provides a side elevational view of the preferred embodiment of the device of the present invention showing in profile the elevational configuration of the device and the various sections of its domed structure as described above. Supine-deterrent 10 is seen to comprise contact annulus 12 and reinforced dome region 14. Reinforced dome region 14 is made up primarily of dome base walls 26, dome top wall 28 and dome intermediate wall 30. Dome intermediate wall 30 presents a more convex surface than dome top wall 28. It is recognized that each of these various regions and sections of the overall hat-shaped domed structure provide some particular function with regard to rigidity and durability.

Associated with contact annulus 12 is perimeter flange 22 which extends beyond the edge of contact annulus 12. Perimeter flange 22 provides a benefit when removing supine-deterrent 10 by presenting a lip for the person to grasp. In conjunction with contact annulus 12, perimeter flange 22 provides strength and presents a relatively flat bottom surface that is more favorable for skin contact, thereby separating the thin edge of the perimeter from the skin.

Although not shown well in FIG. 3, the transitions between perimeter flange 22 and contact annulus 12, as well as between contact annulus 12 and the inside of dome base wall 26, include a smooth radius to minimize pressure concentration on the person's skin.

Airflow aperture 360 is shown in this view positioned on the lower edge of supine-deterrent 10 between adhesive layer 40 and the device of the present invention. When, as described in detail below, the device of the present invention is adhered to the back of the person, some airflow between the interior enclosure defined by the device and the open air exterior of the device is desirable in order to prevent the person from sweating and the resultant discomfort that is typically brought about by the absence of any such airflow. Although the location of airflow aperture 360 results in an opening that tends to partially collapse when operatively positioned on the back of a person, its effective location between the polyethylene dome portion and adhesive layer 40 allows for cost saving in production. With added expense, alternative vent holes may be positioned in other locations such as the peripheral ends of arcuate ridges 18a-18d or dome top wall 28.

Referring again to FIG. 3, angle 380 is shown as the angle between the person's back with supine-deterrent 10 attached and dome base wall 26. Angle 380 is an obtuse angle which provides further support for the dome shape of supine-deterrent 10. The converging character (i.e. its conical nature) enhances structural stability such as with heavier subjects and subjects who move frequently during sleep. This converging character also provides benefits that ease manufacturing.

FIG. 3 also discloses adhesive layer 40 positioned on the underside of contact annulus 12. Adhesive layer 40 represents one of a number of different methods for adhering the supine-deterrent device of the present invention to the back of the person. Adhesive layer 40 may preferably be constructed of double-coated medical tape with a medical skin adhesive compound such as that utilized on bandages and the like, that provides sufficient adhesion to prevent movement or removal of the device from the skin unless a specific and direct force is exerted on the device. The tape comprises hypoallergenic pressure-sensitive adhesives with a high initial adhesion to a very wide range of substrates. In the preferred embodiment, it is important that the device not slide sideways across the skin of the person and remain positioned both in a given location on the person's back and preferably in a given orientation (described in more detail below). The character of adhesive layer 40 must, however, be such as to not cause great discomfort in and of itself when the device is removed when the person finally awakes and no longer has need of the device.

Figure 4A:
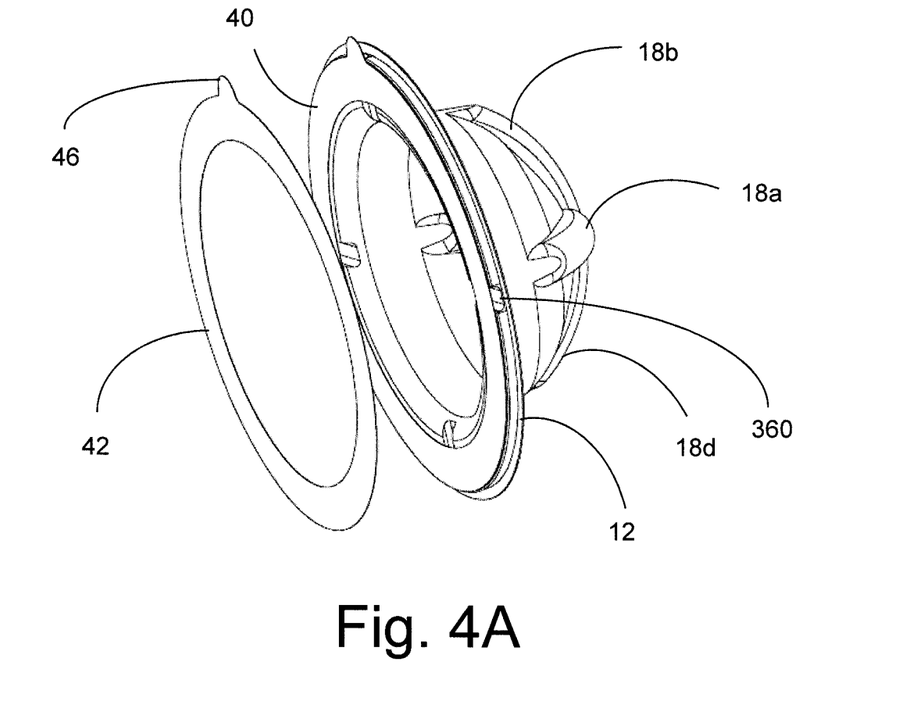
FIGS. 4A & 4B are perspective views of the preferred embodiment 10 of the device of the present invention showing the adhesive system.
Figure 4B:
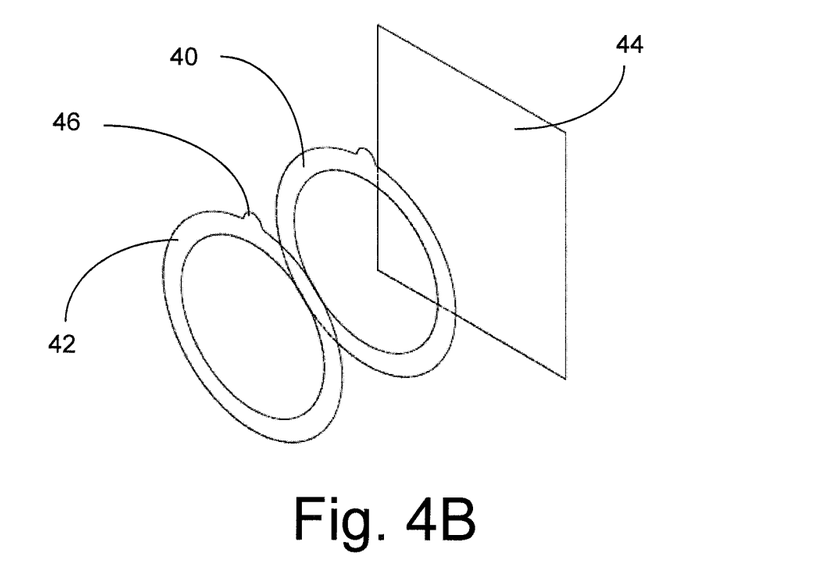

FIGS. 4A and 4B disclose adhesive layer 40. FIG. 4A discloses adhesive protective layer 42 which, when removed by peeling from adhesive layer 40, exposes the double-sided medical tape so that a subject can attach supine-deterrent 10 to the subject's back. Pull-tab 46 is a flap-like extension on adhesive protective layer 42, providing a grasp point for a person to remove adhesive protective layer 42. FIG. 4B provides a perspective view of the sequence of attachment of adhesive protective layer 42, adhesive layer 40 and plastic sheet material 44. During assembly, adhesive layer 40, with the attached adhesive protective layer 42, is applied to the mold of plastic sheet material 44.

Some appropriate adhesive compounds may provide the ability for re-use of the device with the same adhesive layer without the need for the constant replacement of the adhesive material. Some such medical adhesives are known in the art that allow for the temporary removal of a bandage or the like and its replacement after examination of the skin surface beneath the bandage. Such adhesive materials may be utilized in conjunction with the device of the present invention, up to a period of re-use where adhesive layer 40 might preferably be replaced. Various protective steps may be taken to extend the life of the adhesive material, such as the use of storage sheets that may be placed over the adhesive surface when the device is not in use and removed when the device is to be placed into use.

The device of the present invention may preferably be manufactured and sold in packages of two with each device re-usable for as many as 5-10 days without the need to renew the adhesive. Additional double-sided adhesive foam circular rings may be provided within the package so as to allow the person to renew the adhesive layer and further extend the usable life of the device. Various other methods for renewing the adhesive on the underside of the device are anticipated. Although the device may preferably have a complete circular ring of adhesive on the base, this is not essential and an appropriate level of adhesion may be obtained by a number of adhesive patches spaced about the circular perimeter underside of the device.

Figure 5:
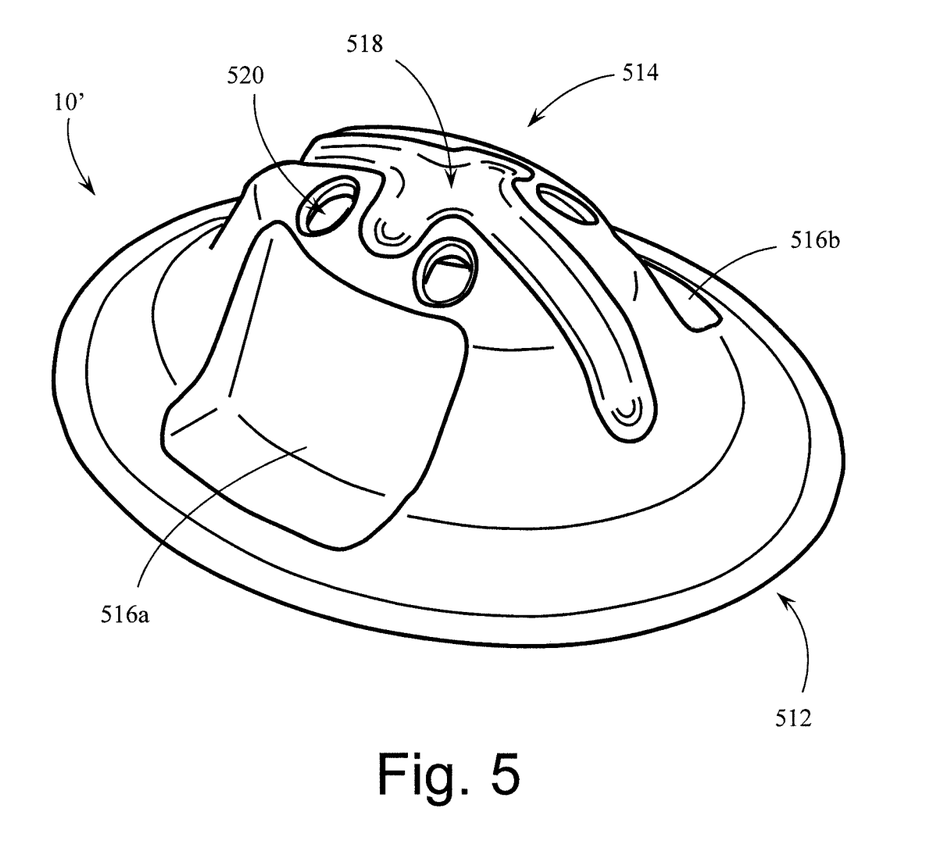
FIG. 5 is a perspective view of an alternative embodiment 10' of the device of the present invention.
Figure 6:
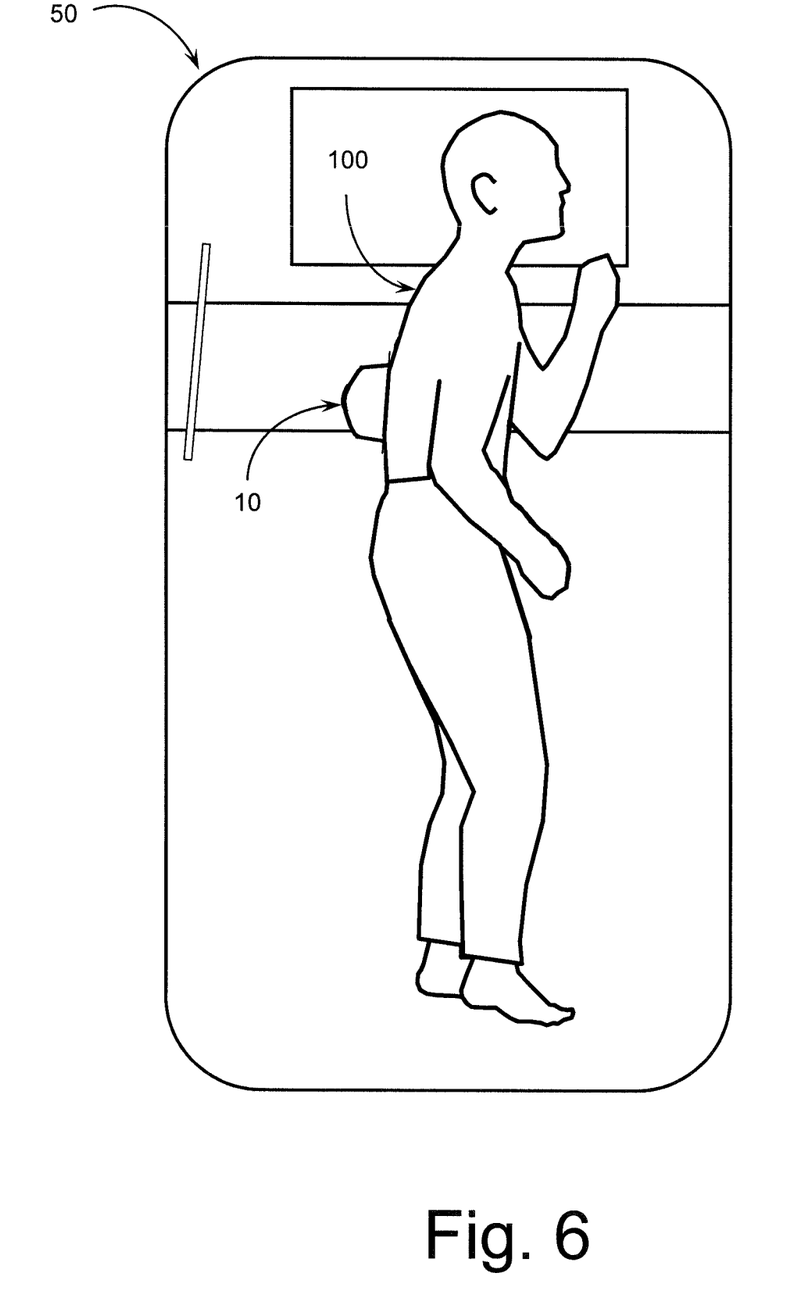
FIG. 6 is a top plan view of the preferred embodiment 10 of the device as positioned on the back of a sleeping subject 100.

Reference is made to FIG. 5 which provides a perspective view of an alternative embodiment of the device of the present invention constructed from a unitary molded plastic material. In the perspective view of FIG. 5, the various external features of the device are disclosed. Supine-deterrent 10' is generally seen to be a helmet-shaped device sized and configured to be removably placed on the back of the person. As described above, the purpose of the device is to consciously or subconsciously deter the person from sleeping on their back. Because snoring while sleeping is frequently associated with the orientation of the sleeper on their back, the device of the present invention serves as a manner of reducing the incidence of snoring while sleeping. The structure of supine-deterrent 10' provides just enough of a conscious or subconscious distraction or discomfort as to cause the person to move into a position where such discomfort no longer exists or occurs. In general, this means moving from a position where the person's back is against the relatively firm surface of the sleeping platform (mattress) to a position where such contact is not being made. Further details regarding this functionality are described in conjunction with FIGS. 7A and 7B below.

FIG. 5 shows in detail the various exterior structural features of supine-deterrent 10' that provide its rigidity, comfort, and ease of positioning and placement for use of the device. The overall helmet-shaped configuration of supine-deterrent 10' includes contact edge region 512 which is a relatively flat ring perimeter region that, on an underside surface (not shown), provides the contact point between the device and the skin surface of the person's back. The manner of adhesively attaching the device of the present invention to the person's back is described in more detail below.

Extending concentrically within contact edge region 512 is reinforced dome region 514 of supine-deterrent 10'. On either side of reinforced dome region 514 are positioned grip indentations 516a and 516b. Positioned near the center of reinforced dome region 514 are rigidity cross-channels 518 and airflow apertures 520. In an alternative embodiment of the present invention, rigidity cross-channels 518 comprise a long cylindrical indentation channel crossed by a short cylindrical indentation channel that together form a cross-shaped recess centered on the apex of reinforced dome region 514 of the device. These rigidity cross-channels 518 primarily provide structural strength to the dome shape of the device. Without such changes in the plane of the surface orientation, and therefore the wall structure of the dome-shaped device, there would be a tendency for the dome shape to collapse when a direct force might be exerted on the apex of the dome. The channels, structured as shown, provide multi-directional structural support to what otherwise would be a flat or simple curve wall structure.

Airflow apertures 520, four orthogonally arranged holes in the alternative embodiment shown in FIG. 5, provide airflow between the interior and exterior of supine-deterrent 10'. When, as described in detail below, the device of the present invention is adhered to the back of the person, some airflow between the interior enclosure defined by the device and the open air exterior of the device is desirable in order to prevent the person from sweating and the resultant discomfort that is typically brought about by the absence of any such airflow.

Grip indentations 516a and 516b are provided on either side of reinforced dome region 514 and serve both the purpose of providing additional structural rigidity to reinforced dome region 514 and providing an easy means for the person to grasp the device, position it and place it appropriately on their back. While the exact placement of the device is not so critical (see discussion below), there is a preference for positioning and placing the device within a region that will most likely encounter the mattress surface when the person turns during sleep into a position that might result in a back-sleeping state. Grip indentations 516a and 516b therefore provide an easy means for handling supine-deterrent 10' while the proper positioning and placement of the device by the person is being carried out.

Figure 8:
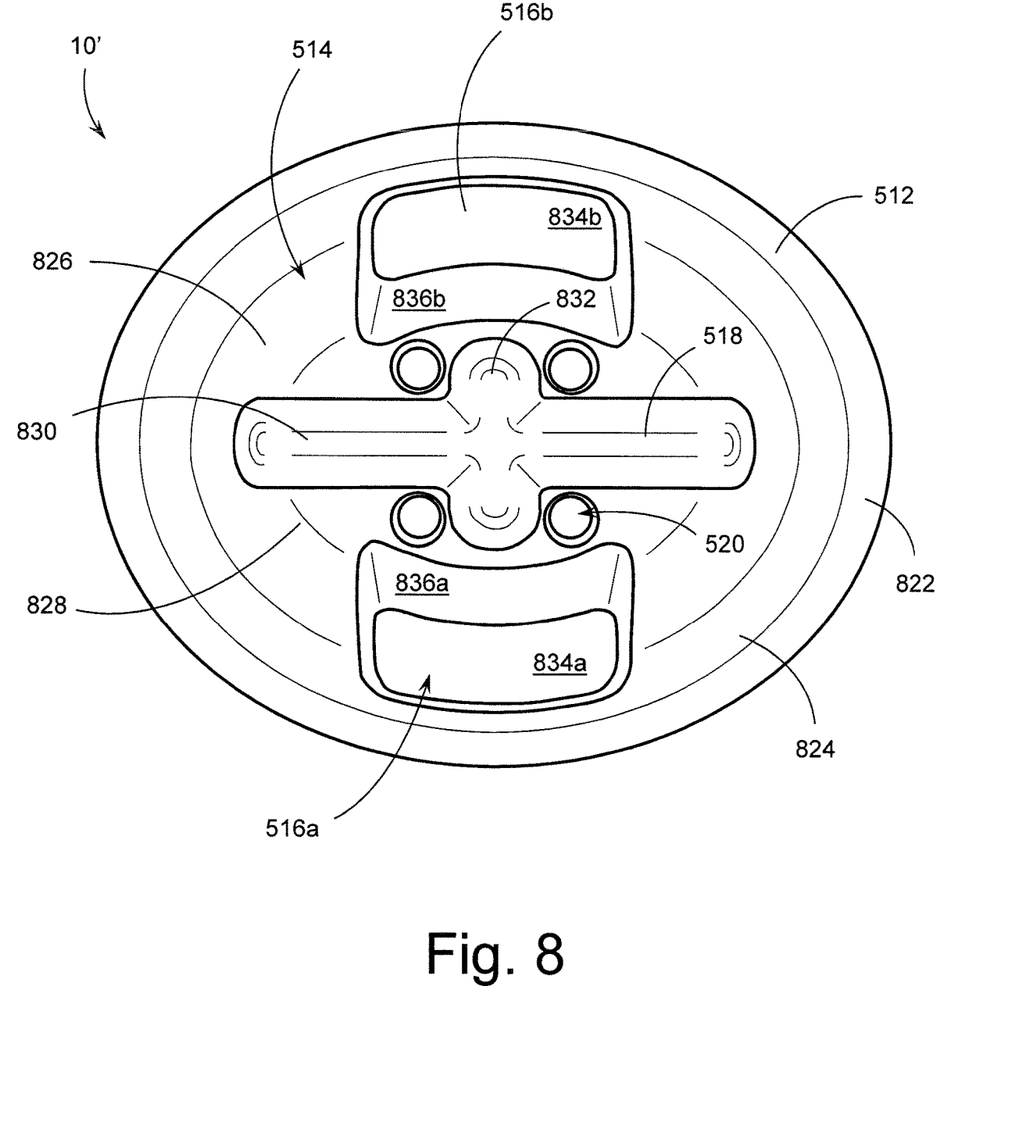
FIG. 8 is a top plan view of the alternative embodiment 10' of the device of the present invention showing the exterior structures of the device.

FIG. 8 is a top plan view of an alternative embodiment of the device of the present invention highlighting in greater detail the structures and contours of the various external features of the device as briefly described in conjunction with FIG. 5. In FIG. 8, supine-deterrent 10' is shown to be constructed from a generally oval-shaped device having contact edge region 512 as well as reinforced dome region 514 as described above. Forming contact edge region 512 are perimeter base 822 and perimeter riser 824. Forming reinforced dome region 514 are dome base walls 826 and dome top wall 828. Rigidity cross-channels 518 are shown as they are positioned and configured within dome top wall 828. Rigidity long channel 830 extends partially across the long axis diameter of oval-shaped supine-deterrent 10' while rigidity short channel 832 extends along the short axis diameter of the oval.

Grip indentations 516a and 516b are shown on either side of dome top wall 828 formed within reinforced dome region 514, primarily within dome base walls 826 and extending to a degree into dome top wall 828. Each grip indentation 516a and 516b comprises a grip wall 836a and 836b and a grip base 834a and 834b, respectively. These grip indentations 516a and 516b comprising the walls and bases as described, provide the person with the ability to grasp the device using (for example) the thumb of the hand in one of the grip indentations, 516a for example, and the forefinger or two fingers of the same hand in the opposing grip indentation, 516b for example. In this manner the person may slightly squeeze the device to grip it firmly for orientation positioning and placement on the person's back.

Referring once again to FIG. 8, airflow apertures 520, numbering four in an alternative embodiment, are positioned on dome top wall 828 in an equally spaced orthogonal manner that optimizes airflow through the device. This airflow results from the apertures being positioned near the apex of the device (away from the skin surface of the person) in a sufficient number as to allow for ordinary (unforced) airflow from the inside of the device to the outside ambient air.

Figure 9:
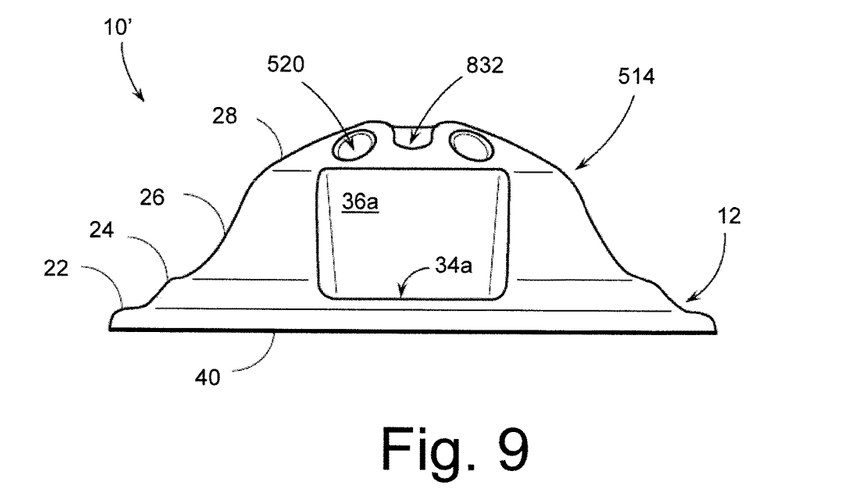
FIG. 9 is a long axis side elevational view of the alternative embodiment 10' of the device of the present invention.

Reference is next made to FIG. 9 which provides a long axis side elevational view of an alternative embodiment of the device of the present invention showing in profile the elevational configuration of the device and the various sections of its domed structure as described above. Supine-deterrent 10' is seen to comprise contact edge region 512 and reinforced dome region 514. Contact edge region 512 is made up of perimeter base 822 and perimeter riser 824. Reinforced dome region 514 is made up primarily of dome base walls 826 and dome top wall 828. It is recognized that each of these various regions and sections of the overall helmet-shaped domed structure provide some particular function with regard to rigidity and durability.

FIG. 9 also discloses from the side view, the configuration of grip indentation 516a with grip base 834a and grip wall 836a. Two of airflow apertures 520 are shown in this view extending across dome top wall 828 to a point where a matched pair of airflow apertures 520 allows for a similar influx and outflow of air from the interior of the device.

Rigidity short channel 832 is visible in this orientation view along the long axis of the oval-shaped supine-deterrent 10'. FIG. 9 also discloses adhesive pad 940 positioned on the underside of perimeter base 822 of contact edge region 512. Adhesive pad 940 represents one of a number of different methods for adhering the supine-deterrent device of the present invention to the back of the person. Adhesive pad 940 may preferably be constructed of a medical skin adhesive compound such as that utilized on bandages and the like, that provides sufficient adhesion to prevent movement or removal of the device from the skin unless a specific and direct force is exerted on the device. In the preferred and alternative embodiments, it is important that the device not slide sideways across the skin of the person and remain positioned both in a given location on the person's back and preferably in a given orientation (described in more detail below). The character of adhesive pad 940 must, however, be such as to not cause great discomfort in and of itself when the device is removed when the person finally awakes and no longer has need of the device.

Some appropriate adhesive compounds may provide the ability for re-use of the device with the same adhesive pad without the need for the constant replacement of the adhesive material. Some such medical adhesives are known in the art that allow for the temporary removal of a bandage or the like and its replacement after examination of the skin surface beneath the bandage. Such adhesive materials may be utilized in conjunction with the device of the present invention, up to a period of re-use where adhesive pad 940 might preferably be replaced. Various protective steps may be taken to extend the life of the adhesive material, such as the use of storage sheets that may be placed over the adhesive surface when the device is not in use and removed when the device is to be placed into use.

The device of the present invention may preferably be manufactured and sold in packages of two with each device re-usable for as many as 5-10 days without the need to renew the adhesive. Additional double-sided adhesive foam oval rings may be provided within the package so as to allow the person to renew the adhesive layer and further extend the usable life of the device. Various other methods for renewing the adhesive on the underside of the device are anticipated. Although the device may preferably have a complete oval ring of adhesive on the base, this is not essential and an appropriate level of adhesion may be obtained by a number of adhesive patches spaced about the oval perimeter underside of the device.

Figure 10:
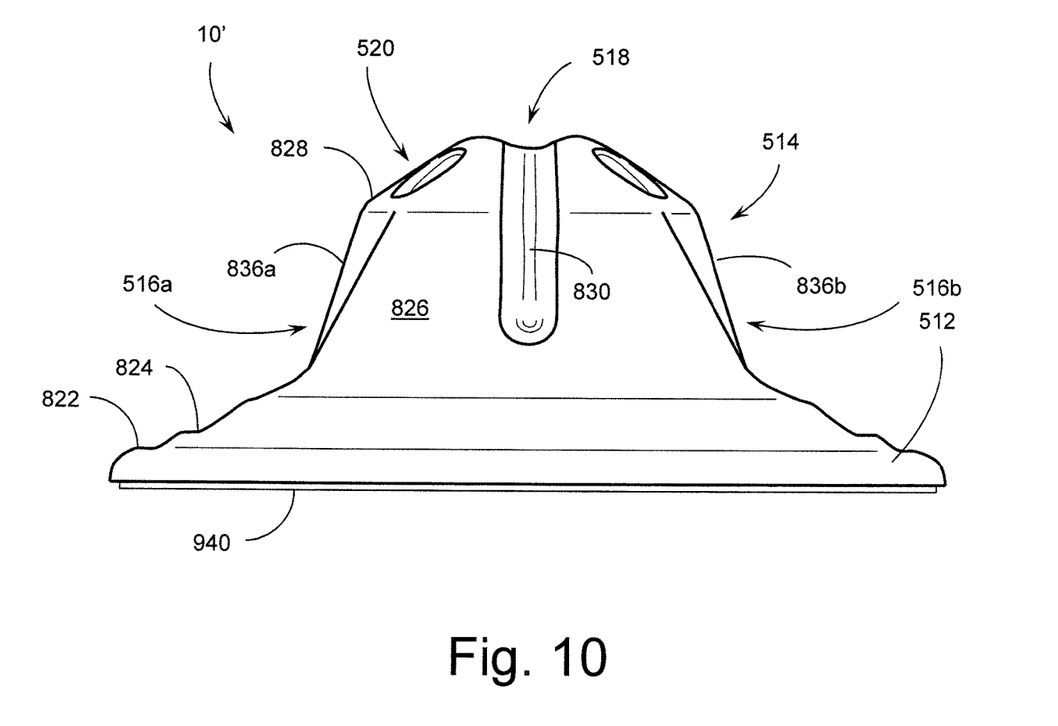
FIG. 10 is a short axis side elevational view of the alternative embodiment 10' of the device of the present invention.

Reference is next made to FIG. 10 which is a view similar to that shown in FIG. 9, but oriented orthogonally (90°). In this view, contact edge region 512 is again shown to comprise perimeter base 822 and perimeter riser 824. Reinforced dome region 514 is again shown to comprise dome base walls 826 and dome top wall 828. Positioned on dome top wall 828 are rigidity cross-channels 518 with rigidity long channel 830 primarily visible in this view.

Grip wall edges 836a and 836b of grip indentations 516a and 516b are also seen in this view. The view of FIG. 10 shows that the grip indentations are primarily established near their base and actually extend outward from dome base walls 826 near their top portions. This again provides an appropriately oriented pair of surfaces for the person to grip the device and position it accurately on the person's back. Perhaps even more importantly, these grip surfaces provide an easy means for the person to grasp and remove the device after use.

The remaining features discussed with regard to FIG. 9 are likewise shown in FIG. 10 and include airflow apertures 520 as well as adhesive pad 940 positioned on the underside of perimeter base 822.

Figure 11:
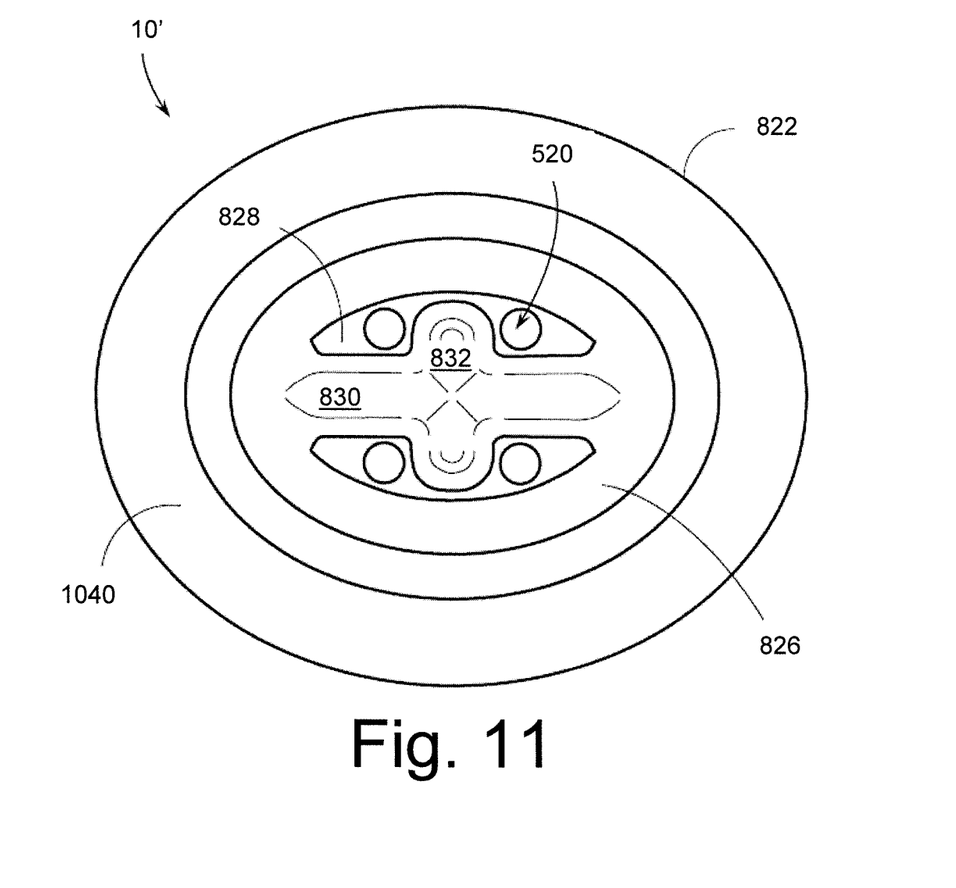
FIG. 11 is a bottom plan view of the alternative embodiment 10' of the device of the present invention showing the interior structures of the device.

Reference is next made to FIG. 11 which is a bottom plan view of an alternative embodiment of the device of the present invention showing the interior structures of the device. From this view it can be seen that the interior structures do not necessarily directly correspond to the configuration of the exterior features, as if the device were simply a formed and shaped thin walled structure. Supine-deterrent 10' in this view of FIG. 11 is shown to again comprise perimeter base 822 on which is positioned adhesive pad 940. Extending interior to perimeter base 822 are dome base walls 826 which generally do coordinate and correspond with the exterior appearances of these same structures.

In a similar manner, dome top wall 828 reflects a portion of its structure as viewed from the exterior of the device, albeit with fewer contours that reflect variations in the thickness of the walled structure (from dome base walls 826 up to dome top wall 828) that are provided, again so as to improve the overall rigidity of the device. In this same manner, rigidity long channel 830 is seen as a cylindrical ridge extending into the interior of the device with rigidity short channel 832 likewise forming a crossing ridge to again structure the apex of the device with greater strength.

Airflow apertures 520 are shown as they extend into the interior of supine-deterrent 10' in order to allow the flow of air from the interior to the exterior ambient air when the device has been placed on the person's back and adhesive pad 940 adheres to the skin of the person's back. Absent airflow apertures 520, adhesive pad 940 would seal off the interior from the exterior ambient air in a way that would confine and contain the natural sweat of the person thereby causing eventual discomfort and possible the release of the adhesive material from the person's back.

Figure 7A:
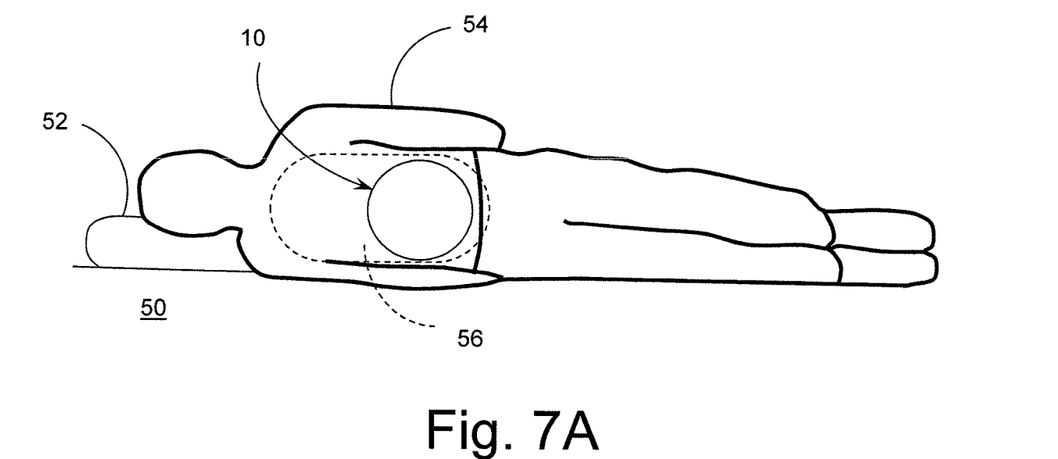
FIGS. 7A & 7B are elevational side views of an individual using the device of the present invention on a sleep support surface (mattress).
Figure 7B:
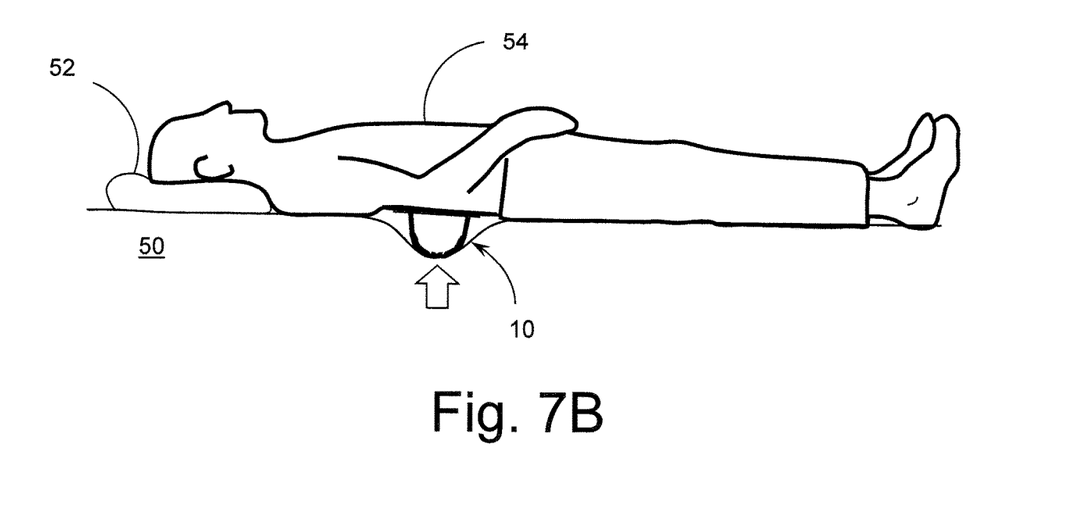

Reference is finally made to FIGS. 7A and 7B which provide elevational side views of an individual using the device of the present invention on a sleep support surface, such as a mattress. Those skilled in the art will recognize that, in addition to the preferred embodiment shown in FIGS. 7A and 7B, other alternative embodiments could also be shown being used in a similar manner. FIG. 7A shows supine-deterrent 10 of the present invention positioned on an individual 54 sleeping on sleep support platform 50 using headrest or pillow 52. Supine-deterrent 10 is preferably placed within a target placement region 56 on the person's back. This target region is defined as that area of the person's back where skeletal support would cause contact between the supine-deterrent 10 and sleep support platform 50 in a manner that would be uncomfortable enough to alert the person, consciously or subconsciously, of the need to turn away from a back sleeping position. In other words, placement of supine-deterrent 10 too far to one side or the other, for example on the shoulders of the person, may not provide enough direct contact between the device and the mattress to give rise to the necessary level of discomfort to deter the person from remaining in the back sleeping position.

FIG. 7B shows what would occur when the person turns into a back sleeping position wherein direct contact between supine-deterrent 10 and sleep support platform 50 is made. As long as the sleep platform (the mattress) is sufficiently firm, there will be enough force upward on supine-deterrent 10, and therefore upward on the back of the individual 54, to create just enough discomfort to deter the person from sleeping on their back. Experience has shown that this level of discomfort is sufficient to re-direct the sleep position of the person without necessarily awakening the person for such purpose. In other words, the subconscious or sleep conditioning effect of the device is more than sufficient to deter the person from turning to or remaining in a back sleep position for any length of time.

A person using a device of the present invention may position and adhere the device on their back prior to laying down on the sleep surface and falling asleep. When its adhesive surface is adhered to the body, the device serves to passively deter the individual from moving into a position that puts weight on the dome of the device, such that it can be adhered in a position to passively deter the individual from moving into an undesired position while sleeping. By adhering the device to corresponding regions of the body, this serves to prevent and minimize nocturnal repositioning and/or unintended weight loading of body parts for subjects who need to avoid as much and, in the case of those prone to snore on their backs, serves to prevent, minimize and deter snoring. Hence, as described above, by adhering the device to a subject's back, it is preferably used to deter an individual from turning onto their back during sleep and thereby deter snoring that often results from a back sleeping orientation. When the person wakes after sleep and exits the sleep surface, they may simply reach around to grasp the device (again as described above) and remove it from their back. The preferred reusable adhesive material may then be temporarily covered by a thin flexible sheet of plastic to prevent the accumulation of dirt and dust on the adhesive surface during non-use.

Although the present invention has been described in conjunction with the above preferred embodiments, those skilled in the art will recognize that certain modifications to the size, structure, and geometric configuration of the device may be made without departing from the spirit and scope of the invention. Although the various features of the device have been described with regard to their function and therefore some manner of their configuration, variations on these configurations are anticipated. While the circular shape of the device, for example, lends itself to greater ease of handling and placement, the shape may just as readily take on a ovoid configuration with little degradation in the functionality of the device. In a similar manner, greater elongation of the device along the long axis of the oval may occur as long as the entire device may still be positioned firmly and flatly against the contours of the person's back.

The size of the device is, of course, variable, but must be large enough to provide the necessary minimal discomfort to deter sleeping on the device and yet must be small enough to adhere to the back securely despite the various contours of the back that naturally occur. The diameter of the preferred embodiment of the device of the present invention is approximately five inches, the diameter at the base of reinforced dome region 14 is approximately three and one-half inches, and the height of the preferred embodiment is approximately two inches. However, those skilled in the art will recognize that such modifications as to geometries and structures are natural variations that still produce a device that achieves the desired function and purpose.

The invention claimed is:

1. A device configured for deterring an undesirable sleeping posture in human subjects, the device comprising:
    a dome;
    a flexible annulus positioned at a base of and integrally formed with the dome, the flexible annulus having a substantially planar lower surface positionable in proximity to skin of a human subject in a region which will deter the human subject from maintaining the undesirable sleeping posture, the flexible annulus being configured to enable conformity relative to a contour of the skin; and
    an adhesive layer comprising a top surface directly contacting the substantially planar lower surface of the flexible annulus and a bottom surface configured to directly contact the skin of the human subject, wherein the adhesive layer has an annulus shape generally corresponding to a shape of the substantially planar lower surface of the flexible annulus and is configured to adhere the flexible annulus to the skin of the human subject,
    wherein the dome comprises a dome base wall, a dome intermediate wall, and a dome top wall, wherein the dome base wall is conical in shape from where it contacts the flexible annulus to where it meets the dome intermediate wall, the dome intermediate wall provides a generally smooth transition between the dome top wall and the dome base wall and is more convex than the dome top wall, and the dome top wall is convex and forms the apex of the dome, and
    wherein a height of said dome is approximately 2 inches and is configured to create physical discomfort for the human subject by generating a force upwardly against the human subject when the human subject is in the undesirable sleeping posture with said dome oriented downward toward a sleeping surface.

2. The device as defined in claim 1, wherein the dome is formed from a sheet of material.

3. The device as defined in claim 2, wherein the dome is molded from a resilient lightweight plastic material.

4. The device as defined in claim 3, wherein the dome is die-stamped on a punch press from sheet stock of amorphous polyethylene terephthalate with a thickness of 0.0175 inches.

5. The device as defined in claim 1, wherein the dome comprises an additional structural feature configured to resist collapsing when a force is exerted upon the dome.

6. The device as defined in claim 5, wherein:
    the additional structural feature is one or more arcuate ridges located on an upper portion of an outer surface of the dome; and
    the one or more arcuate ridges are elevated above the outer surface of the dome.

7. The device as defined in claim 5, wherein:
    the additional structural feature is one or more channels located on an upper portion of the dome; and
    the one or more channels are sunken below an outer surface of the dome.

8. The device as defined in claim 1, wherein the dome has a shape of a spherical section.

9. The device as defined in claim 1, wherein the device further comprises one or more airflow apertures, the one or more airflow apertures allowing for ventilation of a space enclosed between the dome and the human subject.

10. The device as defined in claim 1, wherein:
    a diameter of the base of the dome is approximately three and one-half inches.

11. The device as defined in claim 1, wherein:
    the dome has one or more grip indentations configured to provide additional structural rigidity to the dome and to provide an easy means for a person to grasp.

12. The device as defined in claim 1, wherein:
    a ratio of a diameter of the base of the dome to the height of the dome is approximately 1.75:1.

13. A device configured for deterring an undesirable sleeping posture in human subjects, the device comprising:
    a dome;
    a flexible annulus positioned at a base of and integrally formed with the dome, the flexible annulus having a substantially planar lower surface positionable in proximity to skin of a human subject in a region which will deter the human subject from maintaining the undesirable sleeping posture, the flexible annulus being configured to enable conformity relative to a contour of the skin;
    an adhesive layer comprising a top surface directly contacting the substantially planar lower surface of the flexible annulus and a bottom surface configured to directly contact the skin of the human subject, wherein the adhesive layer has an annulus shape generally corresponding to a shape of the substantially planar lower surface of the flexible annulus and is configured to adhere the flexible annulus to the skin of the human subject; and
    one or more airflow apertures to allow airflow between an interior of the dome and an open-air exterior of the dome,
    wherein the dome comprises a dome base wall, a dome intermediate wall, and a dome top wall, wherein the dome top wall is convex and forms the apex of the dome, and the dome intermediate wall provides a generally smooth transition between the dome top wall and the dome base wall and is more convex than the dome top wall, and
    wherein the dome has a height configured to create physical discomfort for the human subject by generating a force upwardly against the human subject when the human subject is in the undesirable sleeping posture with said dome oriented downward toward a sleeping surface.

14. The device as defined in claim 13, wherein:
    one or more arcuate ridges configured to resist collapsing when a force is exerted upon the dome are located on an upper portion of an outer surface of the dome; and
    the one or more arcuate ridges are elevated above the outer surface of the dome.

15. The device as defined in claim 14, wherein:
each of the one or more airflow apertures is positioned at a peripheral end of one of the one or more arcuate ridges.

16. The device as defined in claim 13, wherein:
one or more channels configured to resist collapsing when a force is exerted upon the dome are located on an upper portion of the dome; and
the one or more channels are sunken below an inner surface of the dome.

17. The device as defined in claim 13, wherein:
the one or more airflow apertures are disposed between the flexible annulus and the adhesive layer.

18. The device as defined in claim 13, wherein the one or more airflow apertures are through holes provided through the dome.

19. The device as defined in claim 13, wherein:
a ratio of a diameter of the device to the height of the dome is approximately 2.5:1.

\* \* \* \* \*